(12) United States Patent
Noda et al.

(10) Patent No.: US 7,690,253 B2
(45) Date of Patent: Apr. 6, 2010

(54) FALL DETECTING METHOD AND FALL DETECTING DEVICE

(75) Inventors: Masaru Noda, Kanagawa (JP); Isao Sakaguchi, Saitama (JP)

(73) Assignee: Hitachi Metals, Ltd., Tokyo (JP)

( * ) Notice: Subject to any disclaimer, the term of this patent is extended or adjusted under 35 U.S.C. 154(b) by 295 days.

(21) Appl. No.: 11/813,576

(22) PCT Filed: Jan. 19, 2006

(86) PCT No.: PCT/JP2006/300706

§ 371 (c)(1),
(2), (4) Date: Jul. 9, 2007

(87) PCT Pub. No.: WO2006/080225

PCT Pub. Date: Aug. 3, 2006

(65) Prior Publication Data
US 2009/0031803 A1    Feb. 5, 2009

(30) Foreign Application Priority Data
Jan. 31, 2005  (JP) ............. 2005-022926
Sep. 29, 2005  (JP) ............. 2005-283537

(51) Int. Cl.
*G01P 15/08*    (2006.01)
*G11B 21/12*    (2006.01)

(52) U.S. Cl. ............. 73/510; 360/75; 702/141

(58) Field of Classification Search ............. 73/510, 73/514.01, 514.35; 340/669; 702/141; 360/75
See application file for complete search history.

(56) References Cited

U.S. PATENT DOCUMENTS

| 5,835,298 | A  | * | 11/1998 | Edgerton et al. ............. 360/75 |
| 5,982,573 | A  | * | 11/1999 | Henze ............. 360/75 |
| 7,191,089 | B2 | * | 3/2007  | Clifford et al. ............. 702/141 |
| 7,248,172 | B2 | * | 7/2007  | Clifford et al. ............. 340/573.1 |
| 7,369,345 | B1 | * | 5/2008  | Li et al. ............. 360/75 |
| 7,395,709 | B2 | * | 7/2008  | Noda et al. ............. 73/510 |

FOREIGN PATENT DOCUMENTS

| JP | 08-032420    |    | 2/1996 |
| JP | 2000-241442  | A  | 9/2000 |
| JP | 2000-249717  | A  | 9/2000 |
| JP | 2002-174641  | A  | 6/2002 |

* cited by examiner

*Primary Examiner*—Helen C. Kwok
(74) *Attorney, Agent, or Firm*—Sughrue Mion, PLLC

(57) ABSTRACT

A fall detecting method and a device for detecting a fall with high accuracy even when an object touches a human or a thing while falling. The fall detecting device has an output detecting part for generating an acceleration detection output after comparing the magnitude of acceleration detected by a three-axis acceleration sensor with a certain threshold, an output interruption correcting part for generating an output interruption corrected acceleration output which is corrected for an interruption when a fall acceleration output recovers within a first predetermined time after the fall acceleration output interrupts, and an output continuation time judging part for generating a fall judgment output when the output interruption corrected acceleration output continues for a second predetermined time longer than the first predetermined time.

9 Claims, 8 Drawing Sheets

ACC. OUTPUT WAVE

OUTPUT INTERRUPTION CORRECTED WAVE

FALL DETECTING METHOD AND FALL DETECTING DEVICE

TECHNICAL FIELD

The present invention relates to a fall detecting method and fall detecting device which can be used for protection against fall of portable electronic apparatuses and the like mounted with magnetic disks.

BACKGROUND ART

It is highly likely that portable electronic apparatuses and the like are dropped by mistake because of characteristics thereof. Portable electronic apparatuses such as a notebook personal computer and a part of digital music players having magnetic disks built therein are particularly delicate to shocks and require protection measures against fall. Such protection measures are described in Patent Document 1 and Patent Document 2. In Patent Document 1, a three-axis acceleration sensor is provided and, when acceleration signals of all three axes indicate small acceleration of substantially zero and the acceleration continues for a certain time, it is judged that a portable electronic apparatus is in free falling, and a magnetic head is moved to a retraction area to prevent breakage of the magnetic disk due to shock at the time of fall and collision. In Patent Document 2, when a magnitude of a composite vector of three-axis accelerations exceeds a certain threshold for 90 milliseconds or more, fall is detected and a magnetic head is moved to a retraction area to prevent breakage of the magnetic disk due to shock at the time of fall and collision.

Patent Document 1: Japanese Patent Laid-Open No. 2000-241442

Patent Document 2: U.S. Pat. No. 5,982,573

DISCLOSURE OF THE INVENTION

Problems to be solved by the Invention

When a portable electronic apparatus or the like starts to slip out of a hand or is falling and comes into contact with a person or an object, the portable electronic apparatus or the like may temporarily deviate from a complete free-fall state. In such a case, in the techniques disclosed in the Patent Documents 1 and 2, fall detection is missed. This is because measurement of time for which small acceleration continues is reset halfway when the portable electronic apparatus or the like comes into contact with the person or the object. When a person nearly drops an object by mistake, the person makes a reflex motion in an attempt to prevent the drop and, therefore, it is extremely highly likely that "incomplete free fall" in which the object temporarily deviates from a complete free-fall state occurs.

The present invention has been devised in view of such circumstances and it is an object of the present invention to provide a fall detecting method and a fall detecting device which can detect fall with high accuracy even when a portable electronic apparatus or the like comes into contact with a person or an object during the fall.

Means for solving the Problems

In a fall detecting method according to the present invention, when a portable electronic apparatus or the like including an acceleration sensor and mounted with a magnetic disk starts fall and comes into contact with something and the fall temporarily stops, if the temporary stop of the fall continues for a certain time (which may be referred to as "first predetermined time"), it is judged that the fall ends at that point, and even if temporary fall stops, if the stop is for a short time, it is judged that the fall continues from the fall which occurs before the temporary fall to make it possible to take measures such as retraction when the continuous fall continues for a time in which the portable electronic apparatus or the like is likely to be damaged (which may be referred to as "second predetermined time". It is accurate to set the second predetermined time to a time obtained by deducting a margin for taking retraction measures from the fall time in which the portable electronic apparatus or the like is likely to be damaged.).

In the fall detecting method according to the present invention, it is preferable that, even if an output from the acceleration sensor attached to the portable electronic apparatus or the like corresponds to fall, when the output is shorter than a certain short time (which may be referred to as "third predetermined time"), it is judged that vibration is applied to the electronic apparatus or the like and measures for coping with the fall are not taken.

A fall detecting method according to the present invention includes the steps of:

measuring acceleration applied to an acceleration sensor using the acceleration sensor at each successive time, and comparing the measured acceleration with a certain threshold to judge whether the measured acceleration is a value corresponding to fall (which may be referred to as "full acceleration") or a value not corresponding to fall (which may be referred to as "non-fall acceleration"), (A) when the acceleration measured at each time is the fall acceleration, setting to an output continuation time a period that the acceleration measured at each time has been successively the fall acceleration, comparing the output continuation time with a second predetermined time, returning to the steps of measuring the acceleration and comparing the measured acceleration with the threshold to judge, until the output continuation time reaches the second predetermined time, and judging fall, when the output continuation time reaches the second predetermined time, and (B) when the acceleration measured at each time is the non-fall acceleration, setting to an output interruption time a period that the acceleration measured at each time has been successively the non-fall acceleration since the acceleration was the fall acceleration just before (the acceleration becomes the non-fall acceleration), and comparing the output interruption time with a first predetermined time, (a) when the output interruption time does not reach the first predetermined time, to correct the output continuation time just before (the acceleration becomes the non-fall acceleration) with the output interruption time, and to return to the steps of measuring the acceleration and comparing the measured acceleration with the threshold to judge, and (b) when the output interruption time reaches the first predetermined time, to judge that the fall stops.

The threshold with which the measured acceleration is compared is set to a value smaller than the gravitational acceleration, the acceleration is judged as the fall acceleration when the acceleration is equal to or smaller than the threshold, and the acceleration is judged as the non-fall acceleration when the acceleration is larger than the threshold. When the portable electronic apparatus or the like mounted with the acceleration sensor is falling, since a motion acceleration and the gravitational acceleration offset each other, theoretically, acceleration is not applied to the acceleration sensor. However, it is possible to prevent an influence of the offset by setting the threshold to 20 to 60% of the gravitational acceleration (9.8 m/s$^2$) and, preferably, about 40% of the gravitational acceleration.

In the fall detecting method according to the present invention, it is preferable that the measured acceleration is regarded as the fall acceleration to correct the output continuation time by adding the output interruption time to the output continuation time just before, and to return to the steps of measuring the acceleration and comparing the measured acceleration with the threshold to judge, when the output interruption time does not reach the first predetermined time in the step of comparing the output interruption time with the first predetermined time.

In the fall detecting method according to the present invention, it is preferable that a period, for which the measured acceleration has successively been the fall acceleration since the acceleration was the non-fall acceleration, is set to a preliminary continuation time, and the preliminary continuation time is compared with a third predetermined time, when the acceleration measured at each time is the non-fall acceleration in the steps of measuring the acceleration and comparing the measured acceleration with the threshold to judge, (a) when the preliminary continuation time does not reach the third predetermined time, to judge that the fall stops, and (b) when the preliminary continuation time reaches the third predetermined time, to set to an output interruption time a period, for which the acceleration measured at each time has successively been the non-fall acceleration, and to proceed to the step of comparing the output interruption time with the first predetermined time.

In the fall detecting method according to the present invention, the acceleration sensor can measure acceleration in each axis direction of three-axis orthogonal coordinate and can compare a square sum or a square root of a square sum of the acceleration measured in each axis direction with the threshold. Alternatively, the acceleration sensor can compare the acceleration measured in each axis direction with the threshold.

When, for example, the portable electronic apparatus or the like comes into contact with a person or an object during fall, an output corresponding to the fall acceleration measured by the acceleration sensor is temporarily interrupted. However, when an interruption time of the output corresponding to the fall acceleration is short and the output is recovered in time shorter than the first predetermined time, the continuation time of the fall is the output continuation time obtained by correcting the output interruption time in that period. Thus, it is possible to judge the output continuation time of the fall acceleration, i.e., the continuation time of the fall without being affected by the interruption of the output corresponding to the fall acceleration and judge the fall with high accuracy even when the portable electronic apparatus or the like comes into contact with a person or an object during the fall. The first predetermined time corresponds to a longest output interruption time in which the interruption of the fall acceleration can be corrected. By setting the first predetermined time to be equal to or shorter than ½ of the second predetermined time, it is possible to make it less easy to cause fall misjudgment due to excess correction of an intermittent small acceleration detection output which occurs under non-full conditions such as vertical vibration.

It is preferable that, as correction of the output continuation time at the time when the output corresponding to the fall acceleration is interrupted, i.e., the output corresponding to the non-fall acceleration is issued for a short time (time shorter than the first predetermined time), the fall is regarded as continuing even while the output is interrupted and the output interruption time is added to the output continuation time before the correction to set the output continuation time before the correction added with the output interruption time as the output continuation time. When the output corresponding to the fall acceleration is issued only for a short time and the fall acceleration disappears after that time, for which the fall acceleration continues is set as the preliminary continuation time and the preliminary continuation time is compared with the third predetermined time shorter than the first predetermined time. Consequently, it is possible to prevent misjudgment when the output corresponding to the fall acceleration is issued only for a short time because of vertical vibration or the like.

A fall detecting device according to the present invention includes:

an acceleration sensor which measures acceleration applied at each successive time, an output detecting means which compares the measured acceleration with a threshold, judges whether the measured acceleration is a fall acceleration corresponding to fall or a non-fall acceleration not corresponding to fall, and issues a judgment output, an output continuation time judging means which receives the judgment output, when the judgment output from the output detecting means corresponds to the fall acceleration, measures a period, for which the judgment output corresponding to the fall acceleration continues, sets the period to an output continuation time and compares the output continuation time with a second predetermined time, and issues a fall judgment when the output continuation time reaches the second predetermined time, and an output interruption correcting means which receives the judgment output, when the judgment output from the output detecting means corresponds to the non-fall acceleration, measures a period for which the output corresponding to the non-fall acceleration has continued since the output was the fall acceleration before, sets the period to an output interruption time, and compares the output interruption time with a first predetermined time, to treat as if the output corresponding to the full acceleration continues, and to add the output interruption time to the output continuation time just before to correct the output continuation time, when the output interruption time does not reach the first predetermined time, and to issue a judgment that a fall stops, when the output interruption time reaches the first predetermined time.

It is preferable that the fall detecting device further includes a preliminary continuation time judging means which sets to a preliminary continuation time a period, for which the output corresponding to the fall acceleration has continued since receiving an output corresponding to the non-fall acceleration just before, and compares the preliminary continuation time with a third predetermined time, (a) to Judge that the fall stops, when the preliminary continuation time does not reach the third predetermined time, and (b) to reset the preliminary continuation time and to transmit the output corresponding to the non-fall acceleration from the output detecting means to the output interruption correcting means, when the preliminary continuation time reaches the third predetermined time.

In the fall detecting device according to the present invention, the output interruption correcting means can include a clock-counter which resets its counter, when an output corresponding to the fall acceleration is received from the output detecting means and measures a period, for which the output corresponding to the non-fall acceleration from the output detecting means has continued. The output interruption correcting means can compare the count of the clock-counter with a count corresponding to the first predetermined time, (a) to treat as if an output corresponding to the fall acceleration continues and to correct the output continuation time by adding the count of the clock-counter to the output continuation time just before, when the count of the clock-counter does not reach a count corresponding to the first predetermined time, and (b) to issue a judgment that the fall stops, when the count of the clock-counter reaches a count corresponding to the first predetermined time.

In the fall detecting device according to the present invention, the output interruption correcting means can include a multi-step delaying means, in which a plurality of delaying means having a delay time shorter than the first predetermined time are connected in series. The output interruption correcting means can issue a logical sum of a delayed tap output from the multi-step delaying means obtained by passing an output from the output detecting means through the multi-step delaying means and the output from the output detecting means as an output of the output interruption correcting means.

In the fall detecting device according to the present invention, the acceleration sensor can measure acceleration in each axis direction of the three-axis orthogonal coordinate, and the output detecting means can compare a square sum or a square root of a square sum of the acceleration in each axis direction measured by the acceleration sensor with the threshold. Alternatively, the output detecting means can compare the acceleration in each axis direction measured by the acceleration sensor with the threshold.

The fall detecting method and the fall detecting device according to the present invention can eliminate the likelihood of overlooking the fall and judge the fall with high accuracy even in a fall state in which the portable electronic apparatus or the like comes into contact with a person or an object during fall and temporarily deviates from free-fall conditions. The effect of the present invention is effective regardless of a calibration method and a detection characteristic of the acceleration detecting means.

Figure 1:
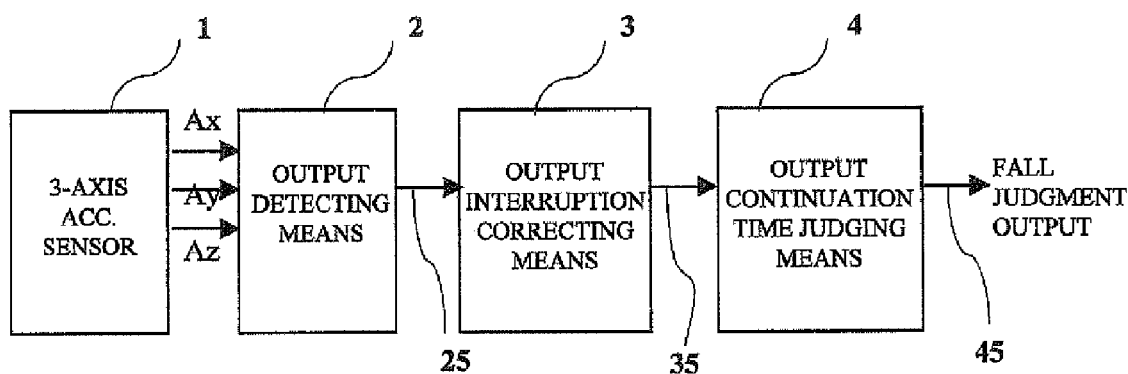
FIG. 1 is a block diagram showing a fall detecting device of EXAMPLE 1 according to the present invention.

EXPLANATION OF REFERENCE NUMERALS 1 (three-axis) acceleration sensor
2 output detecting means
3 output interruption correcting means
4 output continuation time judging means
31, 41 clock counter
36 delaying means

BEST MODE FOR CARRYING OUT OF THE INVENTION

More detailed modes according to the present invention will be explained citing examples.

EXAMPLE 1

Figure 2:
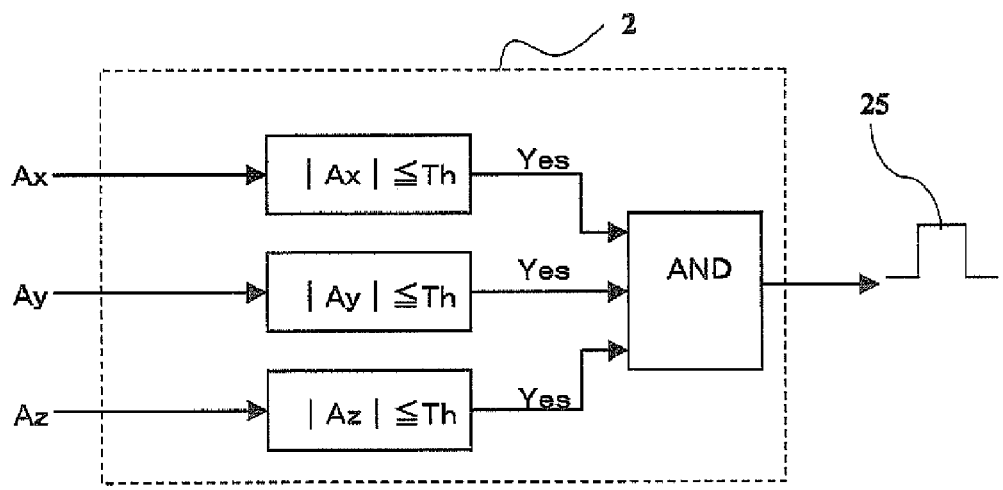
FIG. 2 is a block diagram showing an exemplified structure of output detecting means used in the fall detecting device of EXAMPLE 1 according to the present invention.

A fall detecting device of EXAMPLE 1 according to the present invention is shown in a block diagram in FIG. 1. The fall detecting device includes a three-axis acceleration sensor 1, an output detecting means 2, an output interruption correcting means 3, and an output continuation time judging means 4. The output detecting means 2 adopts a structure shown in FIG. 2. When all of absolute values of accelerations Ax, Ay, A and Az of three axes measured by the three-axis acceleration sensor 1 are equal to or smaller than a threshold Th, the output detecting means 2 outputs an output 25 corresponding to fall acceleration (abbreviated as "fall acceleration"). As shown in FIG. 3, after the fall acceleration disappears from the output 25 of the output detecting means 2, when the fall acceleration recovers within a certain time (a first predetermined time), the output interruption correcting means 3 corrects an output continuation time of the fall acceleration with an interruption time of the fall acceleration and sets a fall acceleration waveform continuing for the corrected output continuation time as an output 35 thereof. In other words, the output interruption correcting means 3 judges that a fall acceleration output has disappeared when interruption of the fall acceleration output continues for the first predetermined time or more, judges that the fall acceleration output is continuing in other cases, and outputs a result of the judgment. The output continuation time judging means 4 generates a fall judgment output 45 when the corrected output 35 continues for a second predetermined time or more.

The second predetermined time is a time for judging fall and is set to make it possible to perform fall judgment before the end of the fall. More strictly, the second predetermined time is set to be shorter than a time obtained by deducting a required time of protection processing after the fall judgment from a fall required time from height set as an object of the fall judgment. However, when the fall judgment time (the second predetermined time) is set excessively short, a probability of misjudging that fall has occurred when a fall acceleration due to non-full such as vertical vibration is detected increases. When the first predetermined time was set to about 10 milliseconds and the second predetermined time was set to about 100 milliseconds, a satisfactory result was obtained.

Figure 3A:
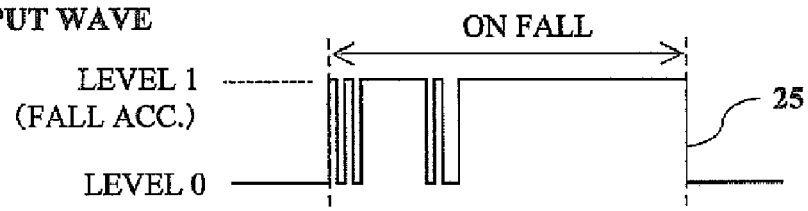
FIGS. 3A and 3B are explanatory views showing examples of acceleration output waves and output interruption corrected waves in EXAMPLE 1.
Figure 3B:
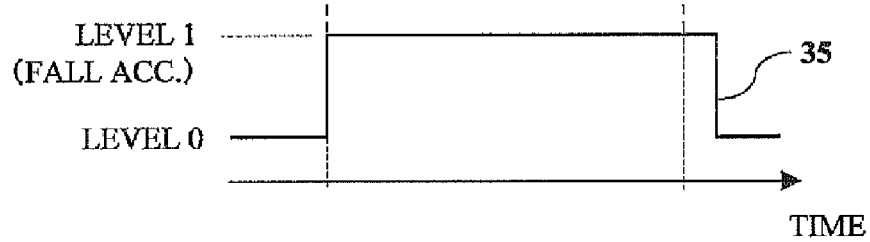

Examples of an acceleration output waveform and an output interruption corrected waveform are shown in FIG. 3. FIG. 3A shows an example of a waveform of the acceleration output 25 outputted from the output detecting means 2 and FIG. 3B shows an example of a waveform of the output 35 corrected by the output interruption correcting means 3. Both FIG. 3A and FIG. 3B schematically show the waveforms. In FIG. 3A, the output 25 at the time when there is no fall acceleration output is displayed as a level 0 and a fall acceleration output is displayed as a level 1. In the waveform shown in FIG. 3A, the fall acceleration output is interrupted twice immediately after start of fall. The interruption of the fall acceleration output occurs because a portable electronic apparatus or the like temporarily deviates from free-fall conditions, for example, when the portable electronic apparatus or the like starts to slip out of a hand and when the portable electronic apparatus or the like comes into contact with a person or an object during the fall. In the acceleration output 35 with the output interruption corrected, as indicated by the waveform shown in FIG. 3B, a state of the level 1 continues until a time set by extending a time from the start of the fall until the end of the fall by the predetermined time set to about 10 milliseconds.

Figure 4A:
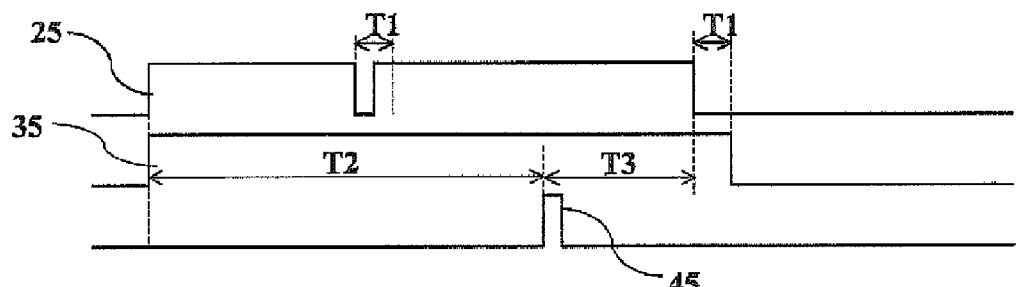
FIGS. 4A and 4B are explanatory views of output at each step in the fall detecting device described in EXAMPLE 1 of the present invention.
Figure 4B:
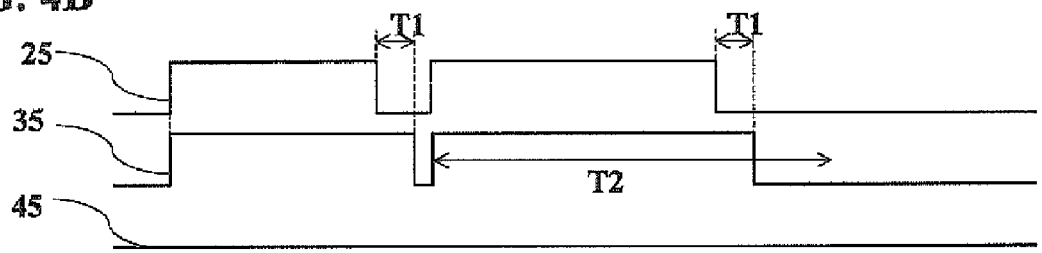

FIG. 4A shows an example in which the output interruption of the acceleration output can be corrected. FIG. 4B shows an example in which the output interruption of the acceleration output cannot be corrected. In FIG. 4, reference numeral 25 denotes an acceleration output from the output detecting mean 2; 35, an acceleration output obtained by correcting the output interruption with the output interruption correcting means 3; 45, a fall judgment output from the output continuation time judging means 4; T1, a first predetermined time; T2, a second predetermined time; and T3, a time which could be spend for protection processing after the fall judgment. In the example shown in FIG. 4A, in the acceleration output 25, although the fall acceleration output is interrupted, since the fall acceleration output recovers in a time shorter than T1, the output interruption is corrected in the corrected acceleration output 35. At time when a continuation time of the corrected acceleration output 35 reaches T2, the fall judgment output 45 is generated. In the example shown in FIG. 4B, the fall acceleration output 25 is interrupted for a time longer than T1 halfway and the output interruption remains in the corrected acceleration output 35. Since the output interruption remains in the corrected acceleration output 35, the continuation time of the corrected acceleration output 35 does not reach T2. Thus, the fall judgment output 46 is not generated. When there is a plurality of times of output interruption shorter than T1, as in the example shown in FIG. 4A, the output interruption is corrected. Consequently, it is possible to detect fall without overlooking the fall even in a case in which the portable electronic apparatus or the like falls while coming into contact with a person or an object.

The output detecting means 2 is not limited to outputting the fall acceleration output 25 when all absolute values of the accelerations Ax, Ay, and Az of the three axes are equal to or smaller than the threshold Th. It is also possible to compare a square sum of three-axis accelerations with the threshold Th to judge the square sum. Alternatively it is also possible to set, as an acceleration output, a logical product of a result of comparing a sum of absolute values of the three-axis accelerations with the threshold Th to judge the sum and a result of comparing all the absolute values of the three-axis accelerations Ax, Ay, and Az with the threshold Th to judge the absolute values. In this way, it is possible to obtain an acceleration output by combining a plurality of systems. It only has to be judged whether a magnitude of acceleration applied to the three-axis acceleration sensor is larger than a predetermined value (a threshold) smaller than the gravitational acceleration.

EXAMPLE 2

Actions of the fall detecting device in EXAMPLE 1 explained with reference to FIGS. 1 to 4 will be explained with reference to a flowchart in FIG. 5.

In order to count an output interruption time of the acceleration output 25 from the output detecting means 2, the output interruption correcting means 3 includes an output interruption time counter. After a fall acceleration disappears from the output 25 of the output detecting means 2, the output interruption time counter counts a time for which the fall acceleration is interrupted and compares the time with the first predetermined time to judge the time. In order to count an output continuation time of the acceleration output 25 from the output detecting means 2, the output continuation time judging means 4 includes an output continuation time counter. In order to judge whether the time for which the fall acceleration from the output 25 of the output detecting means 2 is interrupted is shorter than the first predetermined time, when a count of the output interruption time counter is short compared with the first predetermined time, a count of the output continuation time counter is corrected using the count of the output interruption time counter to set the count as a corrected output continuation time. In the correction of the count of the output continuation time counter, usually, the count of the output interruption time counter is added to the count of the output continuation time counter. The output continuation time counter counts a time for which the fall acceleration continues and compares the count of the output continuation time counter with the second predetermined time to judge the count.

Figure 5:
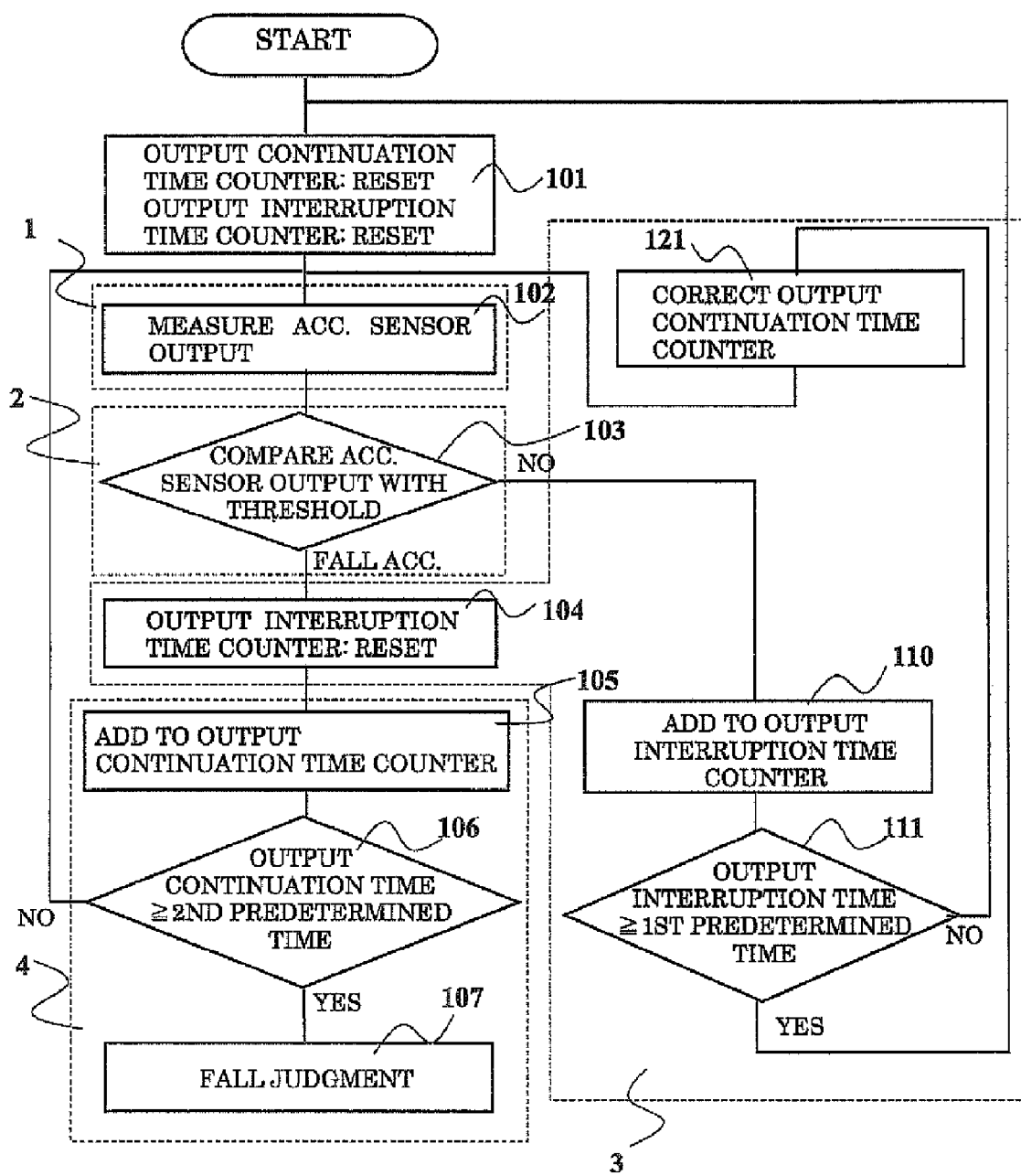
FIG. 5 shows a flow chart of a fall detecting process according to the present invention, described in EXAMPLE 2.

In the flowchart in FIG. 5, the fall detecting device resets the output continuation time counter and the output interruption time counter in the beginning of measurement of a fall acceleration (step 101). The fall detecting device measures an output from the three-axis acceleration sensor 1 at each successive time of a clock (step 102) and compares, in the output detecting means 2, the acceleration sensor output with a certain threshold as explained in EXAMPLE 1 and judges whether the acceleration sensor output is a value corresponding to fall or a value not corresponding to fall (step 103). The output interruption correcting means 3 receives the output 25. When the acceleration measured at each time is a fall acceleration, the output interruption correcting means 3 proceeds to step 104, resets the output interruption time counter, and transmits the output to the output continuation time judging means 4. In the output continuation time judging means 4, the fall detecting device adds a time width of the fall acceleration or one count to the count of the output continuation time counter (step 105) and compares the count of the output continuation time counter with the second predetermined time (step 106). When the count of the output continuation time counter has reached the second predetermined time in step 106, the fall detecting device proceeds to step 107 and performs fall judgment. When the output continuation time counter has not reached the second predetermined time in step 106, the fall detecting device returns to step 102 and measures acceleration at the next time.

When the output is not a fall acceleration in the judgment in step 103, the output interruption correcting means 3 receives the output 25, adds a time width of a non-fall acceleration or one count to the count of the output interruption time counter (step 110), and compares the count of the output interruption time counter with the first predetermined time (step 111). When the count of the output interruption time counter has reached the first predetermined time in step 111, this means that the fall has disappeared. Thus, the fall detecting device returns to the first step for a fall acceleration. When the count of the output interruption time counter has not reached the first predetermined time in step 111, the fall detecting device corrects the count of the output continuation time counter using the count of the output interruption time counter (step 121), returns to step 102, and measures acceleration at the next time.

EXAMPLE 3

Figure 6:
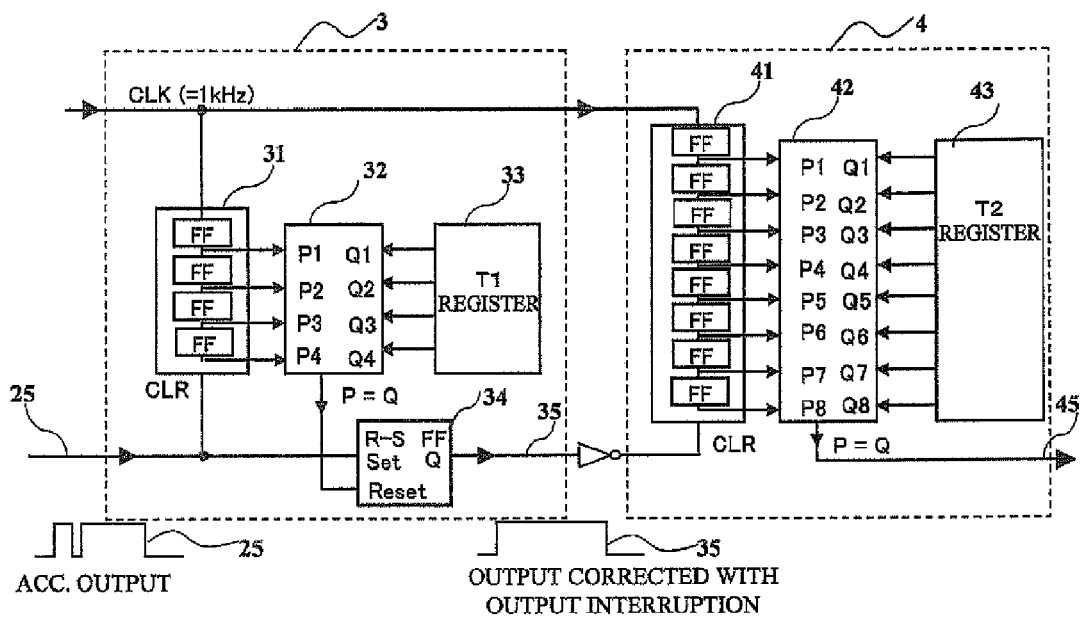
FIG. 6 shows a block diagram of an output interruption correcting means and an output continuation time judging means used in a fall detecting device of EXAMPLE 3 of the present invention.

As a fall detecting device in EXAMPLE 3, a specific example of circuit configurations of the output interruption correcting means 3 and the output continuation time judging means 4 are shown in FIG. 6. The output interruption correcting means 3 includes a clock counter 31, a coincidence comparator 32, a T1 register 33, and an R-S type flip-flop 34. The clock counter 31 corresponds to the output interruption time counter in EXAMPLE 2. The output continuation time judging means 4 includes a clock counter 41, a coincidence comparator 42, and a T2 register 43. The clock counter 41 corresponds to the output continuation time counter in EXAMPLE 2. When the acceleration output 25 rises assuming that the R-S type flip-flop 34 is initially reset, the R-S type flip-flop 34 is set and starts an output Q and continues to be in a state of high (1) until the next reset is applied thereto. The clock counter 31 continues to be cleared in a period in which the acceleration output 25 inputted to a CLR terminal is high. A count value of the clock counter 31 keeps an initial value (usually, zero is the initial value). When the acceleration output 25 is interrupted and falls to low (0), the clock counter 31 is released from the clear and counts up the clock. The coincidence comparator 32 always compares a value corresponding to the first predetermined time stored in the T1 register 33 and a count value of the clock counter 31. When both the values coincide with each other, the coincidence comparator 32 generates an output to thereby reset the R-S type flip-flop 34. When the acceleration output 25 recovers from the output interruption before the count value reaches a value of the T1 register 33, the clock counter 31 returns to the initial value again. Thus, when a continuation time of the output interruption is shorter than the first predetermined time, the R-S type flip-flop 34 is not reset and maintains the output Q high. Consequently, the output 35 with the output interruption corrected is obtained. The clock counter 41 is cleared and continues the initial value in a period in which the output 35 with the output interruption correction is low. When the output 35 rises to high, the clock counter 41 counts up from the initial value. The coincidence comparator 42 always compares a value corresponding to the second predetermined time stored in the T2 register 43 and a count value of the clock counter 41. When both the values coincide with each other, the coincidence comparator 42 generates an output. Consequently, it is possible to generate the fall judgment output 45 when the output with the output interruption corrected continues for the second predetermined time.

EXAMPLE 4

Figure 7:
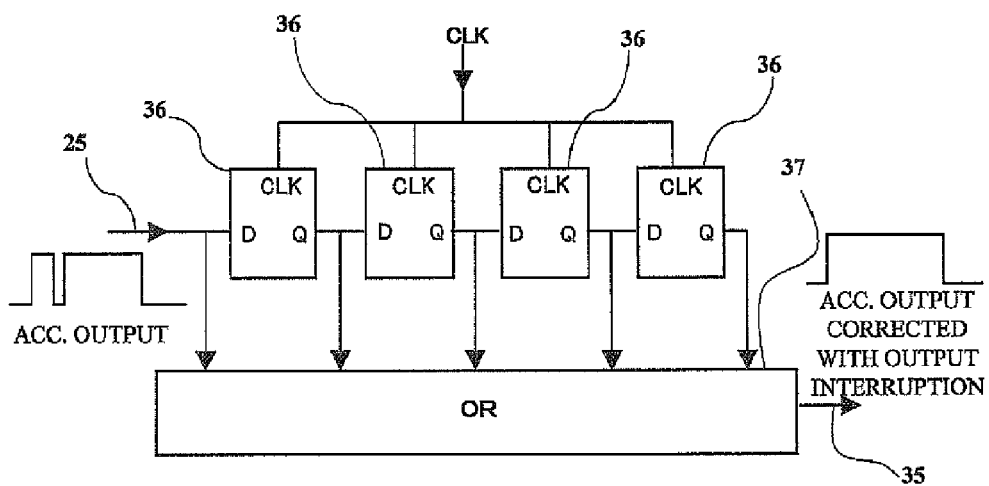
FIG. 7 shows a block diagram of an output interruption correcting means used in a fall detecting device of EXAMPLE 4 of the present invention.

Output interruption correcting means used in a fall detecting device in EXAMPLE 4 is shown in FIG. 7. In FIG. 7, reference numeral 36 denotes D type flip-flops and 37 denotes an OR logical circuit. The D type flip-flops 36 capture binary data, which is applied to D terminals, at time of a clock CLK and output the binary data to Q terminals while holding the binary data until the next clock time. Multi-step delaying means is formed by cascading the D type flip-flops 36 in a plurality of steps. By calculating, in the OR logical circuit 37, a logical sum output of the acceleration output 25 and a plurality of delayed tap outputs obtained by passing the acceleration putout 25 through the multi-step delaying means, it is possible to obtain the output 35 with the output interruption corrected. A time obtained by multiplying a clock period by the number of delayed steps corresponds to the first predetermined time.

EXAMPLE 5

Figure 8:
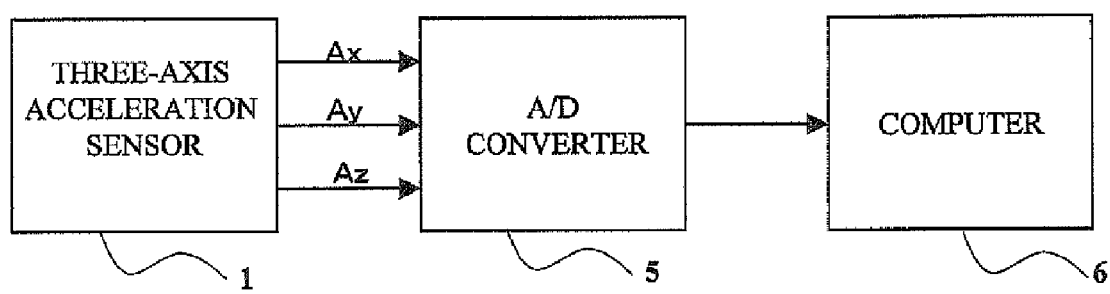
FIG. 8 is a block diagram of a fall detecting device of EXAMPLE 5 according to the present invention.

A fall detecting device in EXAMPLE 5 is shown in FIG. 8. The fall detecting device converts, in an A/D converter 5, the three-axis accelerations Ax, Ay, and Az measured by the three-axis acceleration sensor 1 into digital values and captures the digital values into the microcomputer 6. The microcomputer 6 compares a magnitude of acceleration measured by the three-axis acceleration sensor 1 with a threshold and judges whether the acceleration corresponds to a fall acceleration. The microcomputer 6 executes fall judgment using a result of the judgment in accordance with the flowchart in FIG, 5 explained in EXAMPLE 2. The microcomputer 6 performs, when fall is judged, protection processing for, for example, retracting a head of a hard disk device to a predetermined safe area. The comparison of the measured acceleration with the threshold can be comparison based on the processing algorithm shown as the example in FIG. 2 in EXAMPLE 1. Alternatively, it is possible to compare a value of a square sum of the three-axis accelerations Ax, Ay, and Az or a value of a square root of the square sum with a predetermined threshold and judge the value.

EXAMPLE 6

Figure 9:
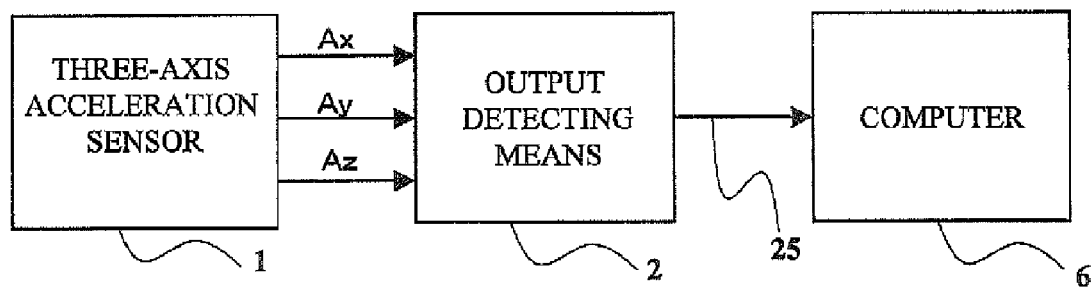
FIG. 9 is a block diagram of a fall detecting device of EXAMPLE 6 according to the present invention.

A fall detecting device in EXAMPLE 6 is shown in FIG. 9. The fall detecting device includes the output detecting means 2 which generates a detection output when the accelerations Ax, Ay, and Az detected by the three-axis acceleration sensor 1 are equal to or smaller than a predetermined threshold smaller than the gravitational acceleration and the microcomputer 6. A processing process executed by the microcomputer 6 judges whether fall has occurred in accordance with steps 104 to 121 of the flowchart in FIG. 5 explained in EXAMPLE 2. The microcomputer 6 performs, when it is judged that the fall has occurred, protection processing for, for example, retracting a head of a hard disk device to a predetermined safe area. An advantage of this example is that an A/D converter is unnecessary.

EXAMPLE 7

A fall detecting method in the case in which a preliminary continuation time judging means 38 is added to the fall detecting devices explained from EXAMPLE 1 to EXAMPLE 6 will be explained with reference to a flowchart in FIG. 10. In the output interruption correcting means 3 in EXAMPLE 1 to EXAMPLE 6, a count of the output interruption time counter is compared with the first predetermined time. However, here, before comparing the output interruption time counter with the first predetermined time, a preliminary continuation time is compared with a third predetermined time to be judged. When vibration having an extremely short period is applied to an acceleration sensor, in order to prevent acceleration caused by the vibration from being judged as fall, the preliminary continuation time is compared with the third predetermined time set shorter than the first predetermined time. When the preliminary continuation time is shorter than the third predetermined time, it is judged that the acceleration is caused by vibration. The output continuation time is not corrected.

Figure 10:
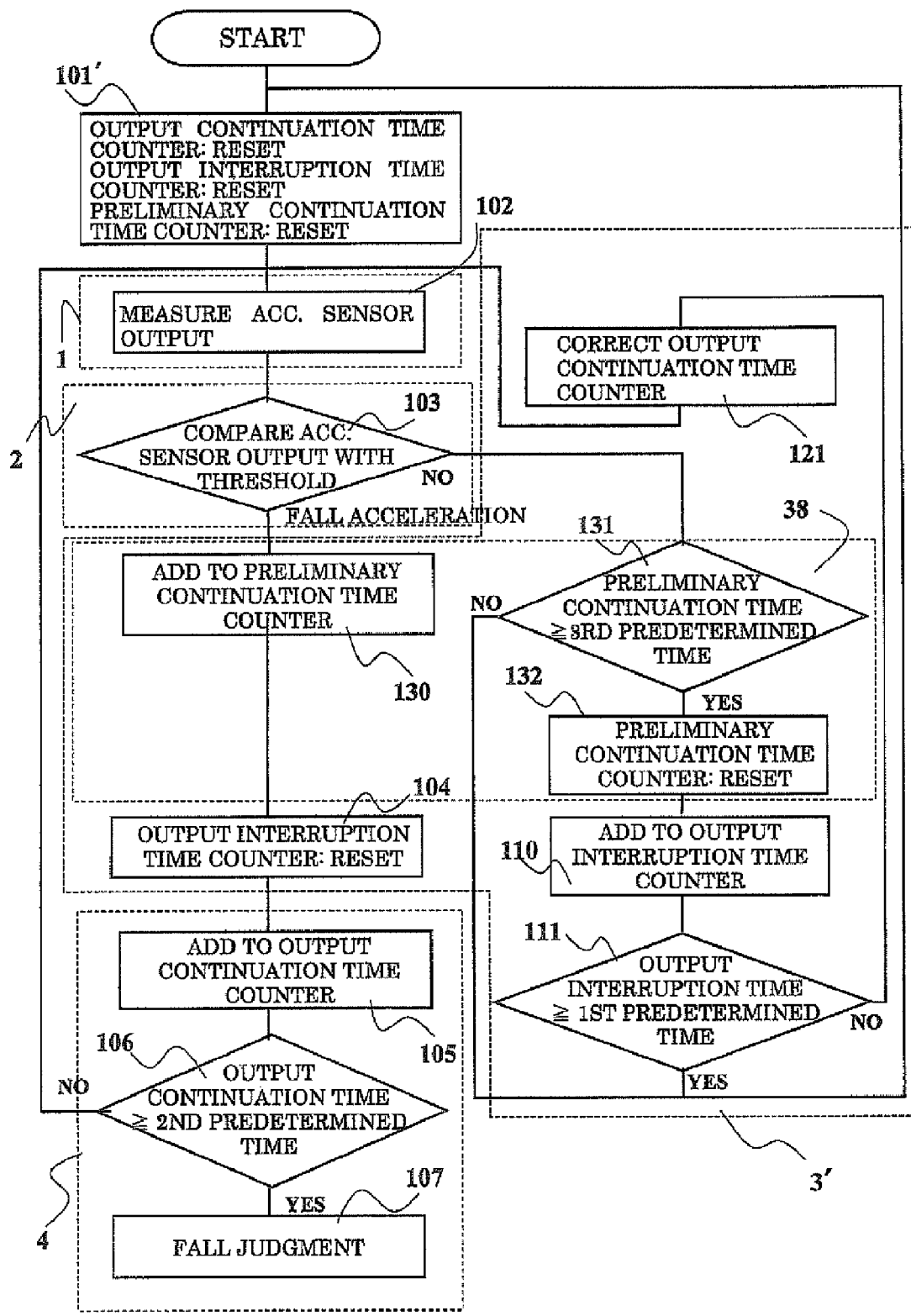
FIG. 10 is a flow chart of a fall detecting process of the present invention described in EXAMPLE 7.

In the flowchart in FIG. 10, a preliminary continuation time counter is provided in order to measure the preliminary continuation time. The fall detecting device resets the output continuation time counter and the output interruption time counter in the beginning of measurement of a fall acceleration and resets the preliminary continuation time counter (step 101'). In step 103, an output interruption correcting means 3' receives a result of judgment on whether an acceleration output in step 103 is a value corresponding to fall or a value not corresponding to fall. When acceleration measured at each time corresponds to a fall acceleration, the fall detecting device proceeds to step 130, adds a time width of the fall acceleration or one count to a count of the preliminary continuation time counter, and proceeds to step 104. Since processes in step 104 and the subsequent steps are the same as those in the flowchart in FIG. 5, explanations of the processes are omitted.

When the acceleration is not a fall acceleration in the judgment in step 103, the fall detecting device compares the count of the preliminary continuation time counter with the third predetermined time (step 131). When the count of the preliminary continuation time counter has reached the third predetermined time in step 131, since this means that the acceleration is not caused by vibration, the fall detecting device resets the preliminary continuation time counter (step 132) and proceeds to step 110. Since processes in step 110 and the subsequent steps are the same as those in the flowchart in FIG. 5, explanations of the processes are omitted.

When the count of the preliminary continuation time counter has not reached the third predetermined time in step 131, since this means that interruption of the acceleration output has occurred after a short time of the fall acceleration, the fall detecting device judges that the acceleration is caused by vibration and returns to the initial stage of the acceleration measurement.

EXAMPLE 8

Figure 11:
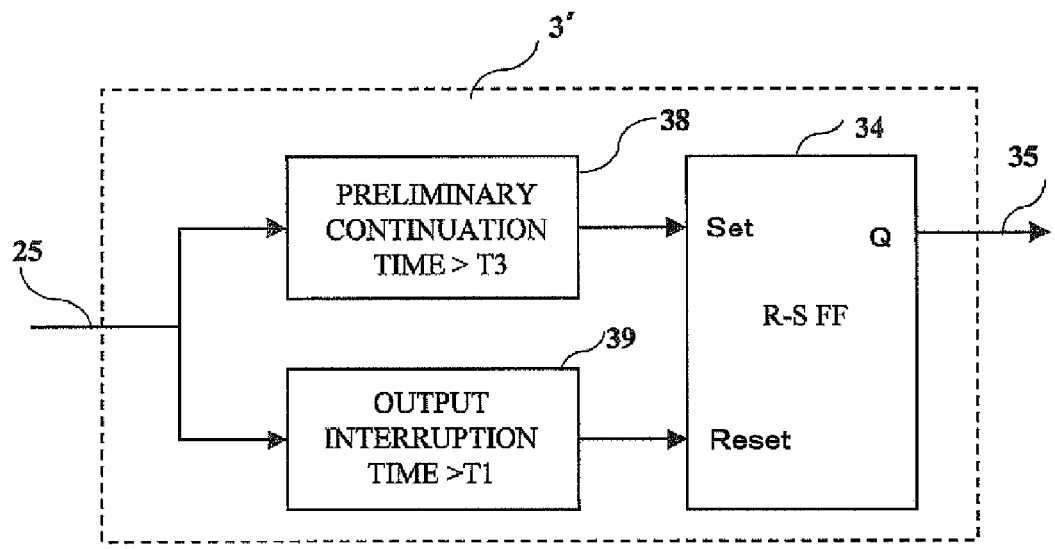
FIG. 11 is a block diagram showing an output interruption correcting means used in a fall detecting device of EXAMPLE 8 according to the present invention.

An output interruption correcting means 3' used in a fall detecting device in EXAMPLE 8 is shown in FIG. 11. The output interruption correcting means 3' includes the preliminary continuation time judging means 38 in order to compare the preliminary continuation time explained in EXAMPLE 7 with the third predetermined time T3. The preliminary continuation time judging means 38 judges whether an output continuation time before interruption occurs in an acceleration output is longer than the third predetermined time T3. When it is judged that the output continuation time is "longer", the preliminary continuation time judging means 38 sets the R-S type flip-flop 34. An output interruption judging means 39 judges whether interruption of an output is longer than a first predetermined time T1. When it is judged that the interruption is "longer", the output interruption judging means 39 resets the R-S type flip-flop 34. The output interruption judging means 39 issues the output 35 with the output interruption corrected to the Q output terminal of the R-s type flip-flop 34.

Figure 12:
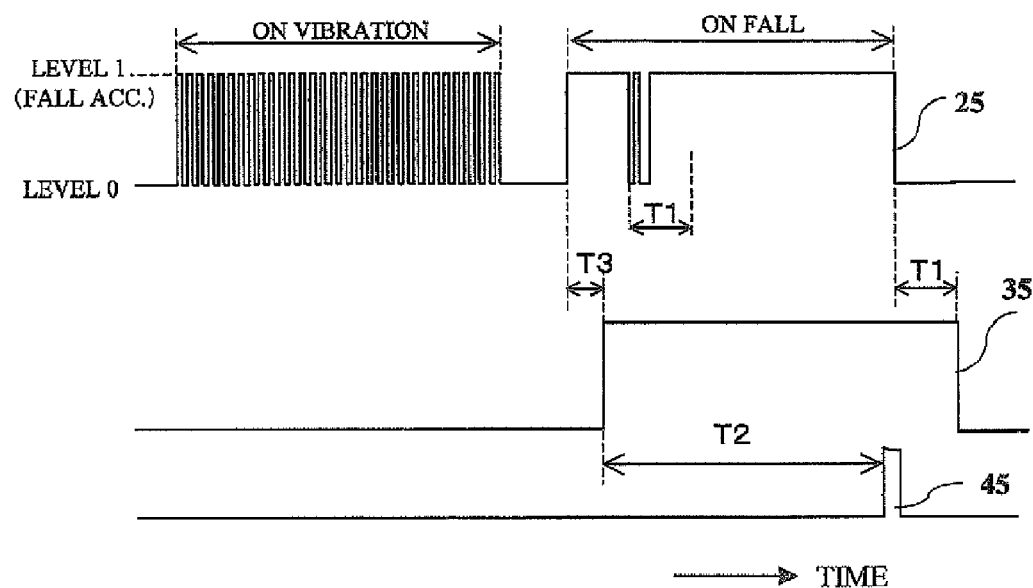
FIG. 12 is a view explaining operations of the fall detecting device of EXAMPLE 8 according to the present invention.

FIG. 12 is a diagram for explaining operations of the output interruption correcting means 3. A waveform of the acceleration output 26 is an example of a wave form, a former half portion of which corresponds to a state during vibration and a latter half portion of which corresponds to a state during fall. In order to deepen understanding, one of extremely rare examples of fall will be explained. When vibration of several hundred Hz is continuously applied to an acceleration sensor with a large amplitude, the acceleration output 25 may have an intermittent waveform shown in FIG. 12. When the fall detecting device does not include the preliminary continuation time judging means 38, it is extremely highly likely that the output interruption correcting means 3' corrects, even for such an intermittent waveform, an output continuation time, generates an output continuation time corrected output when the output continuation time is equal to or larger than the second predetermined time, and misjudges (misdetects) that the continuous vibration of several hundred Hz with the large amplitude is fall. By using the preliminary continuation time judging means 38, since a negative preliminary continuation time judgment result is obtained for the waveform during vibration, the R-S type flip-flop 34 is not set and does not generate a correction output. Therefore, the output interruption correcting means 3' does not misjudge (misdetect) the continuous vibration of several 100 Hz with the large amplitude is fall. The output 35 with the output interruption corrected occurs after the acceleration output 25 due to fall continues for the third predetermined time or more. In FIG. 12, although an output interruption occurs in a time shorter than T1 during fall, this output interruption is corrected and outputted. When this corrected output 35 continues for T2 or more, the fall judgment output 45 is generated. When EXAMPLE 8 is applied to EXAMPLE 5 or EXAMPLE 6, the series of processing explained in EXAMPLE 7 and EXAMPLE 8 is executed by the microcomputer 6.

EXAMPLE 9

Figure 13:
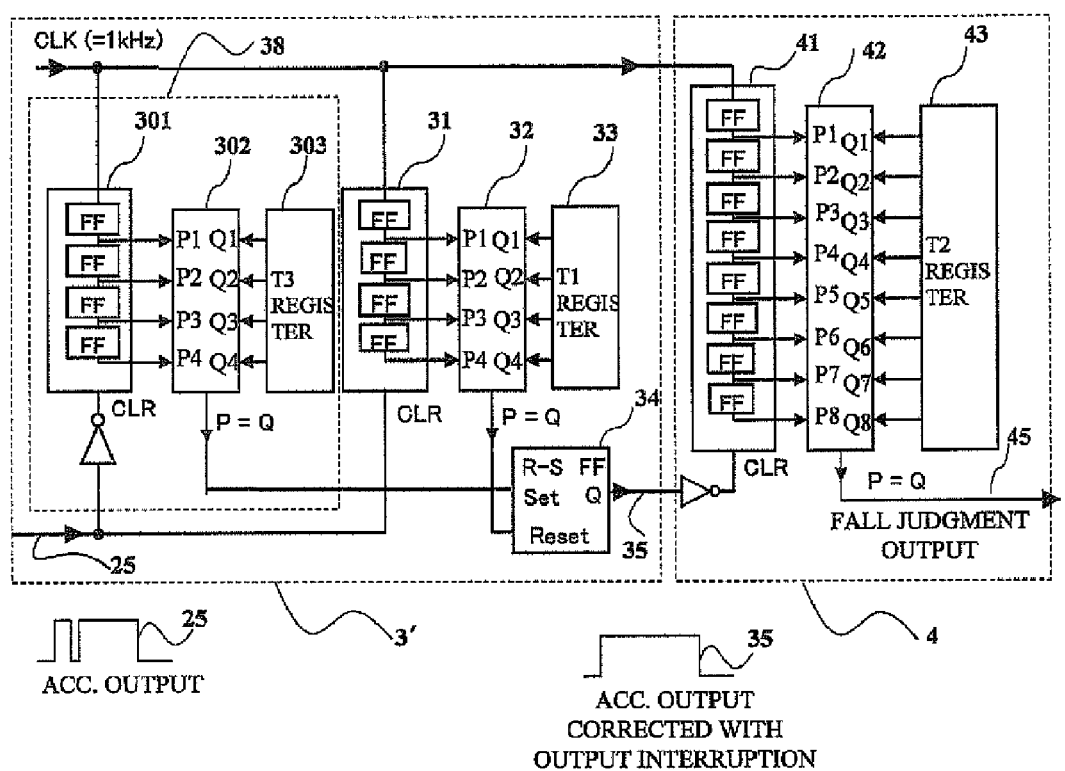
FIG. 13 shows a block diagram of an output interruption correcting means and an output continuation time judging means used in a fall detecting device of EXAMPLE 9 according to the present invention.

A circuit configuration in which EXAMPLE 8 is applied to EXAMPLE 3 is shown FIG. 13 as the output interruption correcting means 3' used in a fall detecting device in EXAMPLE 9. A clock counter 301, a coincidence comparator 302, and a T3 register 303 are added to the fall detecting device (see FIG. 6) in EXAMPLE 3. The clock counter 301 corresponds to the preliminary continuation time counter in EXAMPLE 7. The T3 register 303 stores the third predetermined time. These devices correspond to the preliminary continuation time judging means 38 described in EXAMPLE 8. The clock counter 301 counts a clock while a small acceleration detection output is high. The coincidence comparator 302 generates an output when a count value coincides with a value set in the T3 register 303 and sets the R-S type flip-flop 34. Consequently, operations same as those in EXAMPLE 8 described above are obtained.

As explained above, according to the present invention, it is possible to provide the fall detecting device which is capable of detecting fall without overlooking the fall even when a portable electronic apparatus or the like falls while coming into contact with a person or an object. Moreover, it is possible prevent vibration continuously applied from being misdetected as fall.

INDUSTRIAL APPLICABILITY

As explained above, according to the present invention, it is possible to provide the fall detecting device which is capable of detecting fall without overlooking the fall even when a portable electronic apparatus or the like falls while coming into contact with a person or an object. Moreover, it is possible prevent vibration continuously applied from being misdetected as fall.

The invention claimed is:

1. A fall detecting method comprising the steps of:
measuring acceleration applied to an acceleration sensor at each successive time by the acceleration sensor, and
comparing the measured acceleration with a certain threshold to judge whether the measured acceleration is a fall acceleration corresponding to fall or a non-fall acceleration not corresponding to fall,
(A) when the acceleration measured at each time is the fall acceleration, setting a period, for which the acceleration measured at each time has been successively the fall acceleration, to an output continuation time,
comparing the output continuation time with a second predetermined time,
returning to the steps of measuring the acceleration and comparing the measured acceleration with the threshold to judge, until the output continuation time reaches the second predetermined time, and
judging fall, when the output continuation time reaches the second predetermined time, and
(B) when the acceleration measured at each time is the non-fall acceleration, setting a period, for which the measured acceleration has successively been the fall acceleration since the measured acceleration was the non-fall acceleration just before the measured acceleration becomes the non-fall acceleration, to a preliminary continuation time, and comparing the preliminary continuation time with a third predetermined time,
(a) when the preliminary continuation time does not reach the third predetermined time, judging that the fall stops, and
(b) when the preliminary continuation time reaches the third predetermined time, setting a period, for which the acceleration measured at each time has successively been the non-fall acceleration, to an output interruption time, and comparing the output interruption time with a first predetermined time,
(b-1) when the output interruption time does not reach the first predetermined time,
to correct the output continuation time just before with the output interruption time, and
to return to the steps of measuring the acceleration and comparing the measured acceleration with the threshold to judge, and
(b-2) when the output interruption time reaches the first predetermined time,
to judge that the fall stops.

2. A fall detecting method as set forth in claim 1, wherein the measured acceleration is regarded as the fall acceleration, when the output interruption time does not reach the first predetermined time in the step of comparing the output interruption time with the first predetermined time, to correct the output continuation time by adding the output interruption time to the output continuation time just before, and to return to the steps of measuring the acceleration and comparing the measured acceleration with the threshold to judge.

3. A fall detecting method as set forth in claim 1, wherein the acceleration sensor measures acceleration in each axis direction of three-axis orthogonal coordinate, and a square sum or a square root of a square sum of the acceleration measured in each axis direction is compared with the threshold.

4. A fall detecting method as set forth in claim 1, wherein the acceleration sensor measures acceleration in each axis direction of three-axis orthogonal coordinate, and the acceleration measured in each axis direction is compared with the threshold.

5. A fall detecting device comprising:
an acceleration sensor which measures acceleration applied at each successive time,
an output detecting means which compares the measured acceleration with a threshold, judges whether the measured acceleration is a fall acceleration corresponding to fall or a non-fall acceleration not corresponding to fall, and issues a judgment output,
an output continuation time judging means which receives the judgment output from the output detecting means, when the judgment output corresponds to the fall acceleration, measures a fall period, for which the judgment output corresponding to the fall acceleration continues, sets the fall period to an output continuation time and compares the output continuation time with a second predetermined time, and issues a fall judgment when the output continuation time reaches the second predetermined time,
an output interruption correcting means which receives the judgment output, when the judgment output from the output detecting means corresponds to the non-fall acceleration, measures a non-fall period for which the judgment output corresponding to the non-fall acceleration has continued since the judgment output was the fall acceleration before, sets the non-fall period to an output interruption time, and compares the output interruption time with a first predetermined time,
to treat as if a judgment output corresponding to the fall acceleration continues, and to add the output interruption time to the output continuation time just before to correct the output continuation time, when the output interruption time does not reach the first predetermined time, and
to issue a judgment that a fall stops, when the output interruption time reaches the first predetermined time, and
a preliminary continuation time judging means which receives the judgment output from the output detecting means, sets to a preliminary continuation time a period, for which the judgment output corresponding to the fall acceleration has continued since receiving a judgment output corresponding to the non-fall acceleration just before, when the judgment output corresponds to the non-fall acceleration, and compares the preliminary continuation time with a third predetermined time,
(a) to judge that the fall stops, when the preliminary continuation time does not reach the third predetermined time, and
(b) to reset the preliminary continuation time and to transmit the output corresponding to the non-fall acceleration from the output detecting means to the output interruption correcting means, when the preliminary continuation time reaches the third predetermined time.

6. A fall detecting device as set forth in claim 5, wherein the output interruption correcting means comprises a clock-counter which resets its counter, when a judgment output corresponding to the fall acceleration is received from the output detecting means, measures the non-fall period, for which the output corresponding to the non-fall acceleration from the output detecting means has continued, and compares the count of the clock-counter with a count corresponding to the first predetermined time,
 (a) to treat as if a judgment output corresponding to the fall acceleration continues and to correct the output continuation time by adding the count of the clock-counter to the output continuation time just before, when the count of the clock-counter does not reach the count corresponding to the first predetermined time, and
 (b) to issue a judgment that the fall stops, when the count of the clock-counter reaches the count corresponding to the first predetermined time.

7. A fall detecting device as set forth in claim 5, wherein the output interruption correcting means comprises a multi-step delaying means, in which a plurality of delaying means having a delay time shorter than the first predetermined time are connected in series, and issues a logical sum of a delayed tap output from the multi-step delaying means obtained by passing a judgment output from the output detecting means through the multi-step delaying means plus the judgment output from the output detecting means as an output of the output interruption correcting means.

8. A fall detecting device as set forth in claim 5, wherein the acceleration sensor measures acceleration in each axis direction of the three-axis orthogonal coordinate, and the output detecting means compares a square sum or a square root of a square sum of the acceleration in each axis direction measured by the acceleration sensor with the threshold.

9. A fall detecting device as set forth in claim 5, wherein the acceleration sensor measures acceleration in each axis direction of the three-axis orthogonal coordinate, and the output detecting means compares the acceleration in each axis direction measured by the acceleration sensor with the threshold.

* * * * *